US011741986B2

(12) United States Patent
Vatanparvar et al.

(10) Patent No.: US 11,741,986 B2
(45) Date of Patent: Aug. 29, 2023

(54) SYSTEM AND METHOD FOR PASSIVE SUBJECT SPECIFIC MONITORING

(71) Applicant: Samsung Electronics Co., Ltd., Suwon-si (KR)

(72) Inventors: Korosh Vatanparvar, Santa Clara, CA (US); Tousif Ahmed, San Jose, CA (US); Viswam Nathan, Mountain View, CA (US); Ebrahim Nematihosseinabadi, Santa Clara, CA (US); Md Mahbubur Rahman, San Jose, CA (US); Jilong Kuang, San Jose, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 119 days.

(21) Appl. No.: 16/999,027

(22) Filed: Aug. 20, 2020

(65) Prior Publication Data
US 2021/0134319 A1    May 6, 2021

Related U.S. Application Data

(60) Provisional application No. 62/930,746, filed on Nov. 5, 2019.

(51) Int. Cl.
*G10L 25/66* (2013.01)
*G10L 15/16* (2006.01)

(52) U.S. Cl.
CPC .............. *G10L 25/66* (2013.01); *G10L 15/16* (2013.01)

(58) Field of Classification Search
CPC ......... G10L 25/66; G10L 15/16; G10L 25/30; A61B 5/0823; A61B 5/4803; A61B 5/7267

See application file for complete search history.

(56) References Cited

U.S. PATENT DOCUMENTS 8,589,167 B2 * 11/2013 Baughman .............. G10L 17/26
704/231
10,098,569 B2 * 10/2018 Abeyratne ............. A61B 7/003
(Continued)

FOREIGN PATENT DOCUMENTS

CN      110946554 A     4/2020
EP        3200188 A1     8/2017
(Continued)

OTHER PUBLICATIONS

J. H. L. Hansen and T. Hasan, "Speaker Recognition by Machines and Humans: A tutorial review," in IEEE Signal Processing Magazine, vol. 32, No. 6, pp. 74-99, Nov. 2015 (Year: 2015).*

Lu, L., Liu, L., Hussain, M. J., & Liu, Y. (2017). I sense you by breath: Speaker recognition via breath biometrics. IEEE Transactions on Dependable and Secure Computing, 17(2), 306-319 (Year: 2017).*

(Continued)

*Primary Examiner* — Bhavesh M Mehta
*Assistant Examiner* — Nandini Subramani

(57) ABSTRACT

A method includes obtaining, by an electronic device, an audio segment comprising one or more audio events of a target subject. The method also includes extracting, by the electronic device, audio embeddings from the one or more audio events using an embedding model, the embedding model comprising a trained machine learning model. The method further includes comparing, by the electronic device, the extracted audio embeddings with a match profile of the target subject, the match profile generated during an enrollment stage. The method also includes generating, by the electronic device, a label for the audio segment based on whether or not the extracted audio embeddings match the match profile, wherein the label enables correlation of the audio segment with the target subject for monitoring a health condition of the target subject.

20 Claims, 8 Drawing Sheets

(56) References Cited

U.S. PATENT DOCUMENTS

| | | | |
|---|---|---|---|
| 2009/0119103 A1* | 5/2009 | Gerl | G10L 17/04 704/250 |
| 2012/0220899 A1* | 8/2012 | Oh | A61B 7/003 600/586 |
| 2012/0265024 A1 | 10/2012 | Shrivastav et al. | |
| 2017/0069327 A1 | 3/2017 | Heigold et al. | |
| 2020/0029929 A1* | 1/2020 | Patel | A61B 5/0823 |
| 2020/0035261 A1 | 1/2020 | Mitchell et al. | |
| 2020/0093459 A1* | 3/2020 | Rahman | A61B 5/7282 |
| 2020/0098384 A1 | 3/2020 | Nematihosseinabadi et al. | |

FOREIGN PATENT DOCUMENTS

| | | |
|---|---|---|
| KR | 10-1894722 B1 | 10/2018 |
| KR | 10-2019-0113390 A | 10/2019 |
| KR | 1020190113390 | 10/2019 |
| WO | 2019194843 A1 | 10/2019 |
| WO | 2021081418 A1 | 4/2021 |

OTHER PUBLICATIONS

Sun, X., Lu, Z., Hu, W., & Cao, G. (Sep. 2015). SymDetector: detecting sound related respiratory symptoms using smartphones. In Proceedings of the 2015 ACM International Joint Conference on Pervasive and Ubiquitous Computing (pp. 97-108) (Year: 2015).*
M. Zhang, Y. Chen, L. Li and D. Wang, "Speaker recognition with cough, laugh and "Wei"," 2017 Asia-Pacific Signal and Information Processing Association Annual Summit and Conference (APSIPA ASC), 2017, pp. 497-501 (Year: 2017).*
International Search Report and Written Opinion of the International Searching Authority in connection with International Patent Application No. PCT/KR2020/012214 dated Nov. 30, 2020, 8 pages.
David Snyder, et al.; "Deep Neural Network Embeddings for Text-Independent Speaker Verification"; Proc. Interspeech 2017, pp. 999-1003.
Douglas Reynolds, et al.; "Speaker Verification Using Adapted Gaussian Mixture Models"; Digital Signal Processing, vol. 10, Nos. 1-3, Jan./Apr./Jul. 2000, http://www.idealibrary.com, pp. 19-41.

* cited by examiner

SYSTEM AND METHOD FOR PASSIVE SUBJECT SPECIFIC MONITORING

CROSS-REFERENCE TO RELATED APPLICATIONS AND PRIORITY CLAIM

This application claims priority under 35 U.S.C. § 119(e) to U.S. Provisional Patent Application No. 62/930,746, filed on Nov. 5, 2019, the contents of which are hereby incorporated by reference in their entirety.

TECHNICAL FIELD

This disclosure relates generally to health monitoring systems and methods. More specifically, this disclosure relates to a system and method for passive subject specific monitoring.

BACKGROUND

Recent technological advances in sensing capabilities, wearable devices, and artificial intelligence (AI) are transforming health care by shifting from classical hospitals or clinics to patient centered health care. The transformation enables proactive mobile health and facilitates low-cost unobtrusive solutions for health activity monitoring Passive and mobile health monitoring can be applied to different applications of general health, fitness tracking, and adverse health event prediction. In some cases, the monitoring can be achieved by passively recording a subject's health data, including symptoms and signs demonstrated as audio events. For example, acoustic sensors, with the aid of advanced sound classification methods, can help in identifying lung disease-related early warning signs and symptoms such as cough, sneeze, shortness of breath, and throat clearing. Automatic detection of these audio events and diagnosis of the disease condition extends the capability of passive health monitoring and provides more detailed medically-correlated data for the clinicians.

SUMMARY

This disclosure provides a system and method for passive subject specific monitoring.

In a first embodiment, a method includes obtaining, by an electronic device, an audio segment comprising one or more audio events of a target subject. The method also includes extracting, by the electronic device, audio embeddings from the one or more audio events using an embedding model, the embedding model comprising a trained machine learning model. The method further includes comparing, by the electronic device, the extracted audio embeddings with a match profile of the target subject, the match profile generated during an enrollment stage. The method also includes generating, by the electronic device, a label for the audio segment based on whether or not the extracted audio embeddings match the match profile, wherein the label enables correlation of the audio segment with the target subject for monitoring a health condition of the target subject.

In a second embodiment, an electronic device includes at least one memory configured to store instructions. The electronic device also includes a processor configured when executing the instructions to obtain an audio segment comprising one or more audio events of a target subject. The processor is also configured to extract audio embeddings from the one or more audio events using an embedding model, the embedding model comprising a trained machine learning model. The processor is further configured to compare the extracted audio embeddings with a match profile of the target subject, the match profile generated during an enrollment stage. The processor is also configured to generate a label for the audio segment based on whether or not the extracted audio embeddings match the match profile, wherein the label enables correlation of the audio segment with the target subject for monitoring a health condition of the target subject.

In a third embodiment, a non-transitory computer readable medium contains computer readable program code that, when executed, causes at least one processor of an electronic device to obtain an audio segment comprising one or more audio events of a target subject; extract audio embeddings from the one or more audio events using an embedding model, the embedding model comprising a trained machine learning model; compare the extracted audio embeddings with a match profile of the target subject, the match profile generated during an enrollment stage; and generate a label for the audio segment based on whether or not the extracted audio embeddings match the match profile, wherein the label enables correlation of the audio segment with the target subject for monitoring a health condition of the target subject.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic appcessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MM) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

Figure 1:
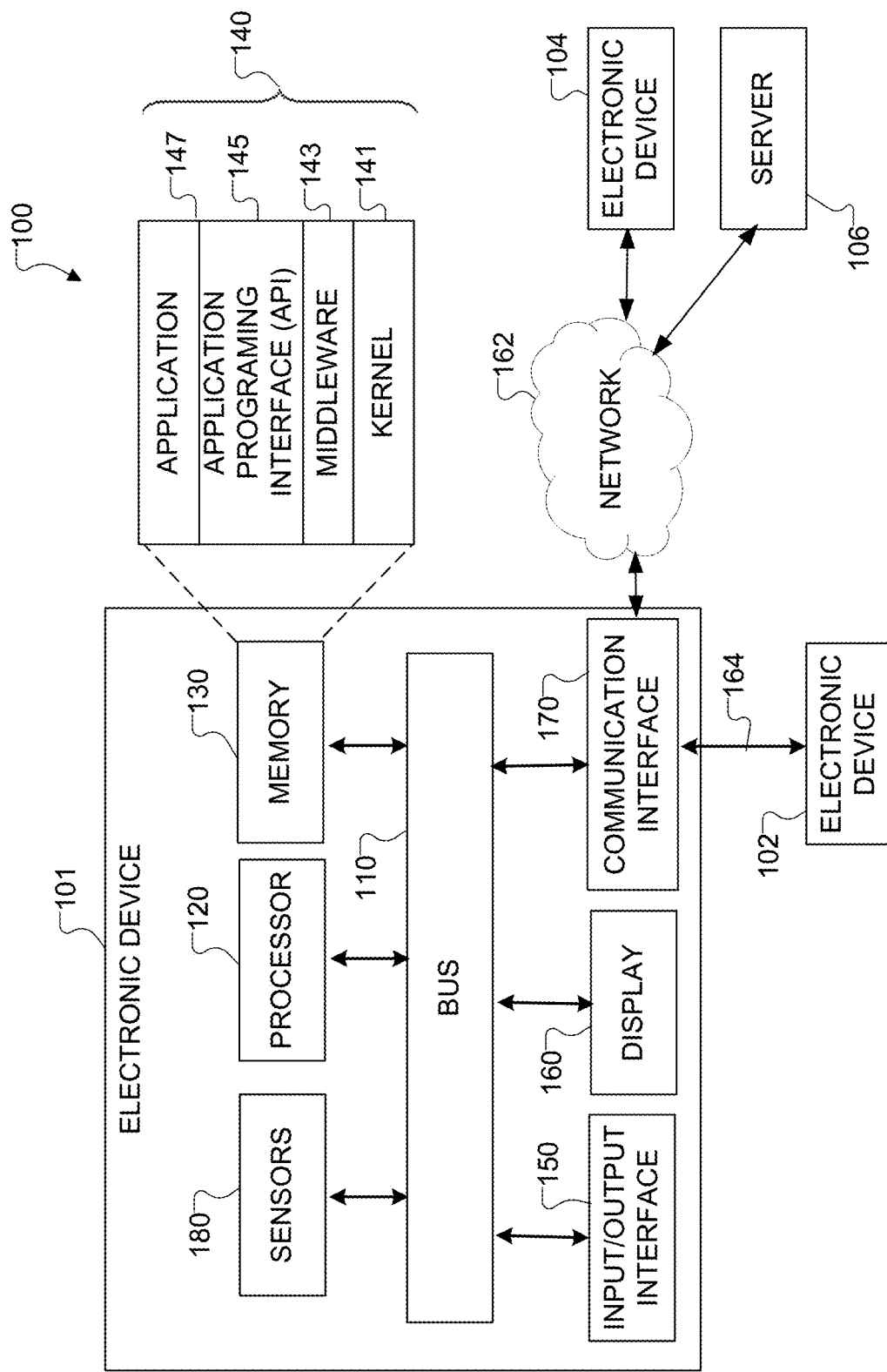
FIG. 1 illustrates an example network configuration in accordance with this disclosure.

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

Recent personal mobile health monitoring systems leverage audio data captured by a microphone to monitor symptoms and signs of disease conditions. The audio data can correspond to an event such as a cough, speech, a sneeze, and the like. For example, passively captured coughs can be leveraged to estimate the severity of lung obstruction in a subject dealing with a pulmonary condition. The collected audio segments can be analyzed to provide an estimation of the subject's health condition or severity of their underlying disease. Monitoring and tracking of the condition can help medical experts to early detect and prevent severe conditions or optimally decide on a prescription and a recovery plan.

Methods of mobile health monitoring that leverage audio-based digital biomarkers depend on reliable audio data from the subjects for health diagnosis, analysis and prediction. In an uncontrolled recording environment, the microphone captures audio from any sources and individuals in the vicinity; thus, all audio events (e.g., cough, speech, etc.) including those from surrounding individuals may be detected and collected. The detected audio of other individuals could then be incorrectly considered into a health analysis or disease diagnosis of the subject by predictive algorithms or clinicians. Misdiagnosis of subject's health, especially in the case of pulmonary conditions such as COPD or asthma, could have serious adverse effects due to both harmful medication use and increased costs for patients.

Conventional techniques for subject-specific audio event detection or subject verification techniques typically require a large set of sample data for a specific target audio event and specific subject to create a personal model. However, the necessary amount of data may not be available or difficult to collect, which makes model creation challenging. This scenario has been seen in studies where cough samples are required from a subject diagnosed with a chronic respiratory disease. It has been observed that an attempt to produce more than 30 seconds or roughly 10 samples of cough may cause inconvenience for the subject, or in some cases, lead to exacerbation or an asthma attack.

Furthermore, the personal model may be prone to the daily changes in subject condition. In other words, the audio characteristics of the audio segments from the target subject may vary over time due to changing health conditions of the subject. The changes in the audio characteristics may cause the subject verification methods to have higher false negatives.

In summary, personal health monitoring which requires passive audio collection from subjects poses the following problems: lack of data regarding the identity of the individual producing the audio events (which can lead to collection of audio events from background individuals without consent and/or misprediction of disease condition and misdiagnosis caused by feeding wrong data), limited availability or difficulty in collection of audio event data to create a personal model, and performance of the personal model being prone to the changing condition of the subject. Thus, passively collecting reliable audio from a specific subject is a major challenge hindering accurate mobile health monitoring. The problem can be generalized to any health-related audio, e.g., cough, speech, throat clearing, wheeze, sneeze, and the like.

To address these and other issues, embodiments of this disclosure provide systems and methods for subject monitoring using audio collection in which audio segments are captured only from specific target subjects. The disclosed monitoring systems and methods are capable of targeting one or more types of audio events for recording from the specific subjects. The systems and methods can be implemented and applied on one or more smart devices, such as smart phones, wearables, hearables, smart speakers, and the like. Moreover, the disclosed embodiments enable collection of audio from multiple specific subjects simultaneously on the same smart device. As described in greater detail below, the disclosed embodiments include a number of advantageous features, including event-independent audio-based subject verification, physiologically-correlated subject-distinctive audio embeddings, cross-event match profile creation, and resiliency and adaptiveness to changing conditions of the subject.

FIG. 1 illustrates an example network configuration 100 in accordance with this disclosure. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 145 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the HMD and operate in a virtual reality mode. When the electronic device 101 is mounted in the electronic device 102 (such as the HMD), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
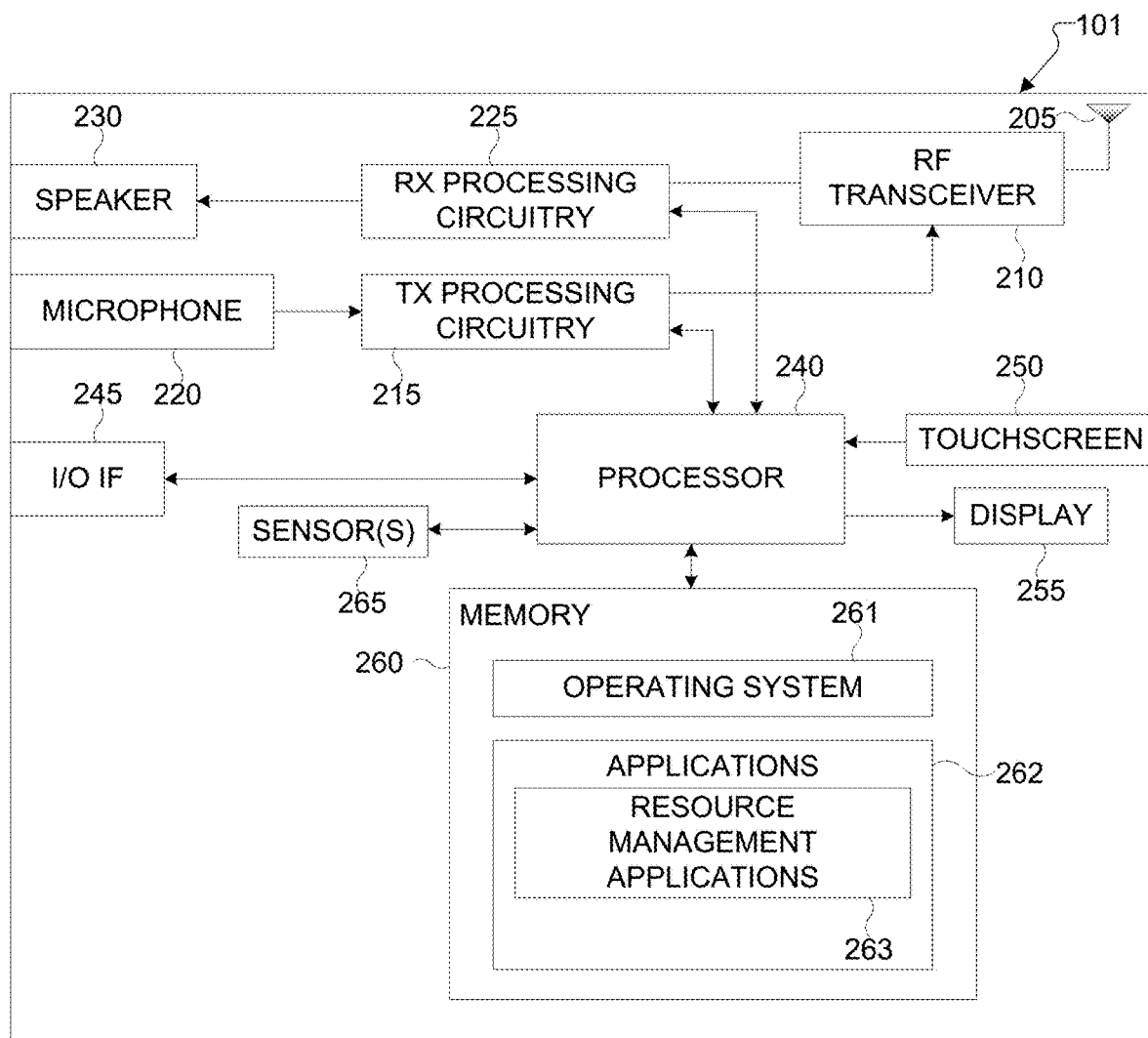
FIG. 2 illustrates an example electronic device in accordance with this disclosure.

FIG. 2 illustrates an example electronic device 101 in accordance with this disclosure. The electronic device 101 could represent one or more of the electronic devices 101, 102, or 104 in FIG. 1. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260. The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing.

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor 240 can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
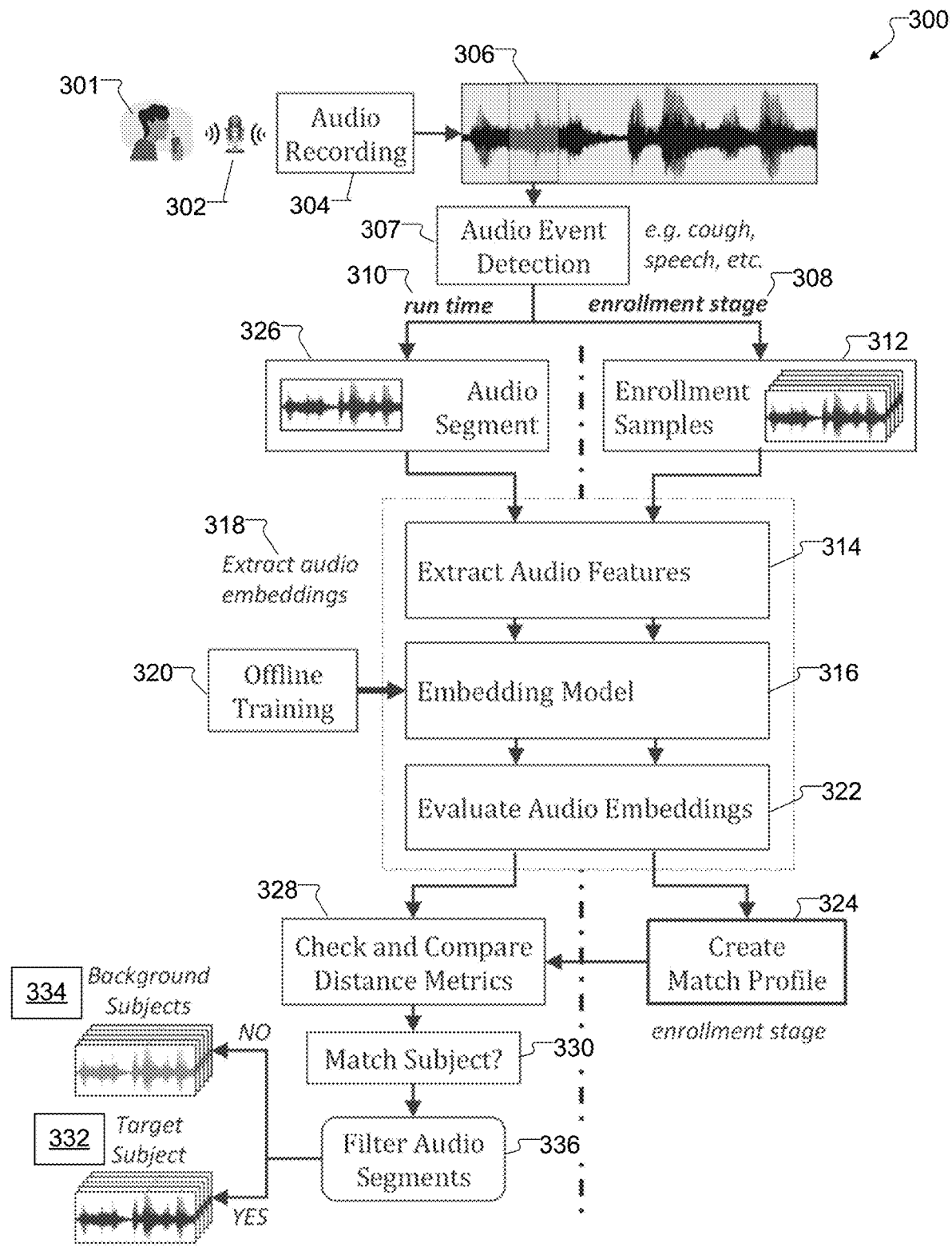
FIG. 3 illustrates an example process for passive subject specific monitoring in accordance with this disclosure.

FIG. 3 illustrates an example process 300 for passive subject specific monitoring in accordance with this disclosure. For ease of explanation, the process 300 is described as involving at least one electronic device (such as the electronic device 101 of FIG. 1). However, the process 300 could be used with any other suitable device or system without departing from the scope of this disclosure.

As shown in FIG. 3, a microphone 302 or other audio sensor is used to record an audio recording 304 for an arbitrary period of time. For example, the electronic device can use a built-in microphone 302 to record audio associated with a subject 301, who may be a user of the electronic device. The audio can include speech spoken by the subject 301 and/or people in proximity to the subject 301, non-speech sounds generated by the subject 301 and/or people in proximity to the subject 301, background noises and speech that occur around the subject 301, or a combination of these. The process 300 integrates an event-independent audio-based subject verification process, which can be performed during an enrollment stage 308 and at run time 310. Depending on whether the electronic device is performing the enrollment stage 308 or is operating at run time 310, the audio recording 304 can include different elements.

During the enrollment stage 308, the audio recording 304 includes audio of the subject 301 that is recorded for a specific duration. The audio may contain samples 312 of one or more specific audio events 306 that can be detected during an audio event detection operation 307. An audio event is the class of a short audio segment produced by the subject 301, such as a cough, speech, a sneeze, and the like. The enrollment samples 312 are processed by the electronic device to extract their spectral audio features 314. One or more audio embeddings 318 that are distinctive for the subject 301 are extracted using an embedding model 316. Each audio embedding 318 comprises a vector of scalar values extracted from the audio segment to verify whether or not the audio belongs to the subject 301. The embedding model 316 is a machine learning model that is trained and optimized by an offline training operation 320 using a separate training dataset to capture and learn correlations between the audio recording 304 and unique physiological structures of the subject 301.

Extracted audio embeddings 318 from the enrollment samples 312 are evaluated during an evaluation operation 322 to create a match profile 324 that is personalized for the subject 301. The personalized match profile 324 is later used at run time 310 to passively check and verify whether each audio segment belongs to the subject 301.

At this stage, the match profile 324 or the audio embeddings 318 can be transformed for another target audio event different from the audio event of the subject 301. This is referred to as cross-event profile creation, which will be described in greater detail below. This feature enables the process 300 to collect and verify one or more events of audio using none or limited samples of the target audio event at the enrollment stage 308.

The match profile 324 is aggregated and evaluated from the audio embeddings 318 and formulated as a matrix $MP_e$, as shown by the following:

$$MP_e = \begin{bmatrix} p_{11} & \cdots & p_{1m} \\ \vdots & \ddots & \vdots \\ p_{n1} & \cdots & p_{nm} \end{bmatrix} \quad (1)$$

where each of the matrix elements ($p_{11} \ldots p_{nm}$) is a scalar value correlated with unique characteristics concealed in the audio samples of the audio event (e) from the subject 301. In addition, a list of match profiles can be created by enrolling multiple specific subjects in order to collect or verify their audio individually and simultaneously on the same device.

At run time 310, one or more audio events 306 are passively detected and extracted from another audio recording 304 collected at run time 310. Each audio segment 326 containing the audio event(s) 306 is processed to extract audio features 314 and audio embeddings 318, using the embedding model 316 that was trained during the enrollment stage 308, or a corresponding transformer model (in case of cross-event profile creation).

Extracted audio embeddings 318 are compared with the match profile 324 created during the enrollment stage 308. This can include evaluating and checking one or more distancing metrics 328 (e.g., Cosine, Euclidean, Manhattan, and the like) between the two vectors.

Furthermore, a likelihood ratio test $\Lambda(X)$ can be implemented to calculate the likelihood of the audio segment 326 belonging to the distribution and profile of the subject 301 as compared to any background subject. In some embodiments, the likelihood ratio test $\Lambda(X)$ can be calculated according to the following:

$$\Lambda(X) = \log \rho(X|MP_e^{target}) - \log \rho(X|MP_e^{background}) \quad (2)$$

where $\log \rho(X|MP_e^x)$ is the likelihood function created based on the match profile 324, either for the subject 301 or a pre-defined population of background subjects in a universal background model (UBM). This can be achieved by using a Gaussian Mixture model (GMM) or another existing unsupervised learned model. In a scenario where multiple subjects generate audio at the same time, the process 300 can reject the audio for each of the subjects since the audio does not correlate with any of their match profile distributions. This allows the process 300 to filter noisy audio that would corrupt prediction of audio-based analyses in later stages or processes.

If the vector of audio embeddings 318 extracted from each audio segment 326 matches the match profile 324, or falls within a distribution from the subject 301 with high probability, the audio segment 326 is labeled as a match 330. That is, one or more "match" labels 332 are generated and associated with the audio segment 326. Conversely, if the vector of audio embeddings 318 does not match the match profile 324, the audio segment 326 is considered to be not a match, and one or more "no match" labels 334 are generated and associated with the audio segment 326. The evaluated subject identity labels 332, 334 are extracted for each audio segment 326. Each audio segment 326 matching the subject 301 can be filtered out using a filtering operation 336, and processed for further analysis such as health monitoring, or health prediction and tracking, of the subject 301.

In the process 300, the determination of the match 330 is performed passively based on the short audio segment 326 without interaction or prior trigger from the subject 301. Event-independency of the subject verification is due to a combination of the physiologically-correlated, subject-distinctive audio embeddings 318 and cross-event match profile creation.

The audio embeddings 318 are used to create the match profile 324 from the enrollment samples 312, and to verify the passively-collected audio segments 326. The audio embeddings 318 are evaluated using the embedding model 316 based on extracted spectral audio features 314 from the audio segments 326. The embedding model 316 is structured to process and transform the audio features 314 to the audio embeddings 318 that have one or more of the following optimization objectives:

Distinction among different subjects (i.e., minimizing the categorical cross entropy).

Correlation with physiological structures of the subject 301 (i.e., correlation between audio embeddings 318 across multiple audio events 306).

Consistent against changes in condition of the subject 301 (i.e., correlation between audio embeddings 318 across multiple conditions).

The embedding model 316 is based on a neural network architecture that is trained by the offline training operation 320 using a separate training dataset to capture and learn application-specific audio features 314 with the above-mentioned optimization objectives.

Figure 4:
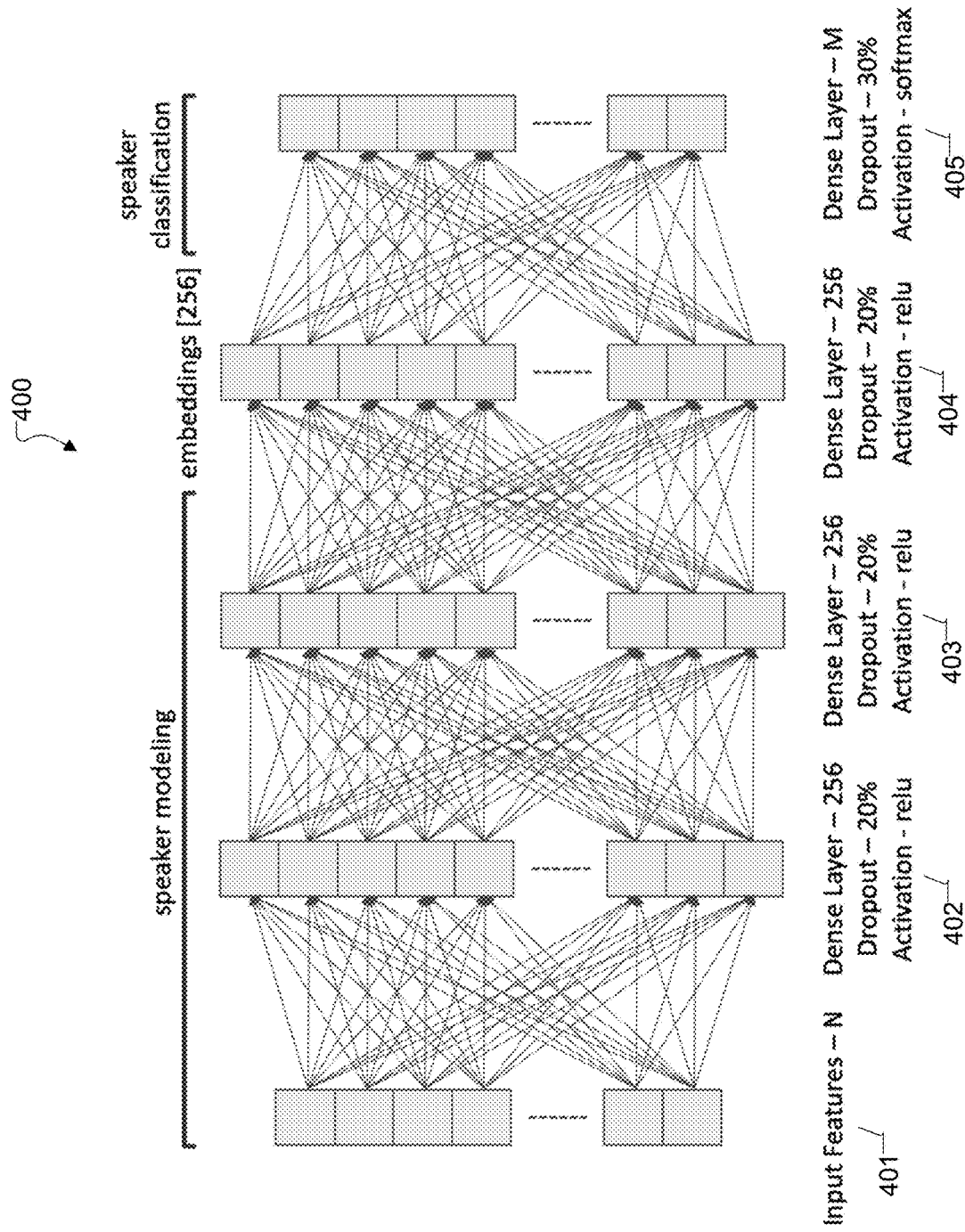
FIG. 4 illustrates an example neural network structure that can be used in the process of FIG. 3 in accordance with this disclosure.

FIG. 4 illustrates an example neural network structure 400 that can be used to extract the audio embeddings 318 and distinguish the subject 301 from other subjects. As shown in FIG. 4, the neural network structure 400 includes an input layer 401, multiple intermediate layers 402-404, and an output layer 405. While the neural network structure 400 is shown with three intermediate layers 402-404, this is merely one example; other embodiments could include other numbers of intermediate layers.

The audio embeddings 318 are selected such that they are not dependent on any contextual information of the audio, making the embedding model 316 consistent among different recording scenarios (i.e., different content) and duration of audio. The embedding model 316 is optimized and regularized with an objective of maintaining accuracy and embedding values consistent for multiple audio samples recorded in different subject conditions and events. Therefore, the audio embeddings 318 can capture characteristics that are correlated with the physiological and vocal cord structure of the subject 301, rather than the current condition and event.

During the offline training operation 320 of the embedding model 316, a dataset is created containing audio samples for different audio events (e.g. cough and speech) from multiple subjects in various conditions. The different subject conditions may be either due to passage of time or proactively by giving a drug or medication to one or more subjects. The dataset is further split into training and test sets to put aside a set of subjects for cross-subject validation in order to prevent biasing the model towards specific subjects.

Figure 5:
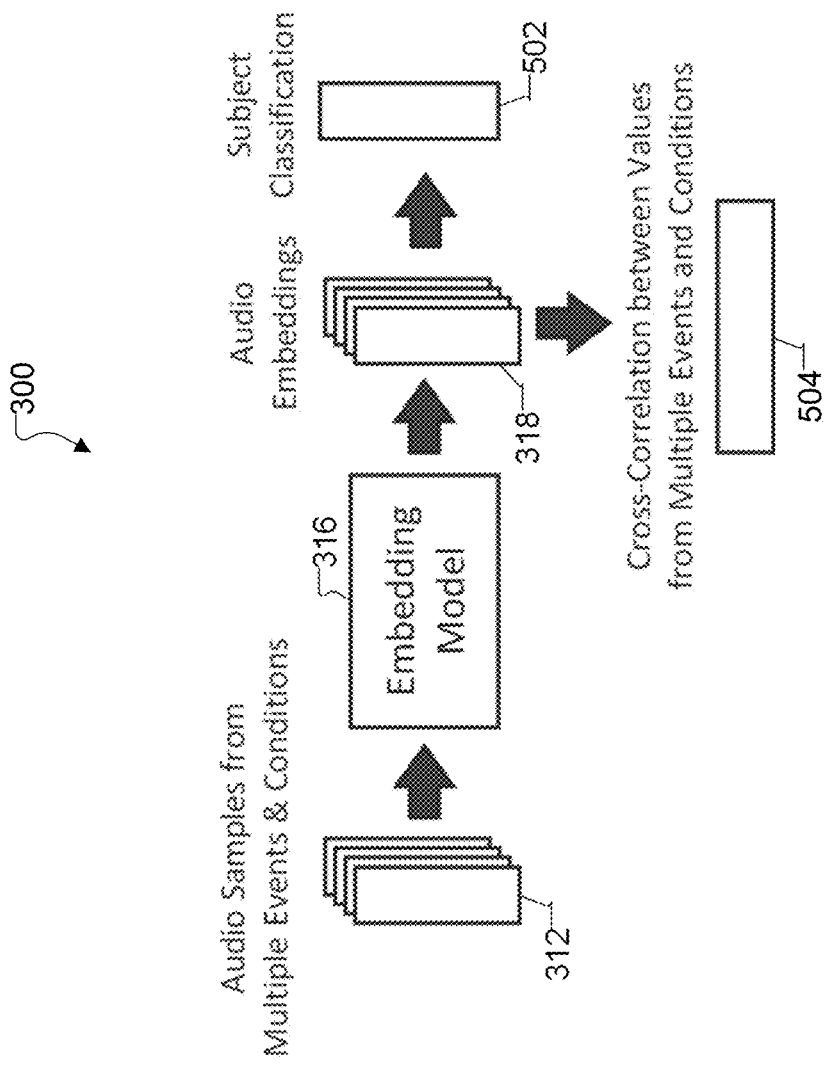
FIG. 5 illustrates further details for training an embedding model using the process of FIG. 3 in accordance with this disclosure.

FIG. 5 illustrates further details of training the embedding model 316 using the process 300. As shown in FIG. 5, one objective of training the embedding model 316 is for subject classification 502. The audio embeddings 318 are extracted from the neurons in the embedding model 316 (e.g., the output layer 405 of the neural network structure 400 in FIG. 4). An objective of categorical cross entropy is defined at the output layer 405 to increase the distinction between subjects using the audio embeddings 318 (as described in greater detail below in conjunction with FIG. 7).

In addition to subject classification 502, another parallel layer of optimization, referred to as cross-correlation 504, is defined where the audio embeddings 318 are compared for different audio events and subject conditions. In this optimization objective, the cross-correlation of the evaluated audio embeddings 318 are maximized in order to optimize the embedding model 316 to focus on physiologically-correlated audio features 314 common across different events and conditions. The training is performed either jointly, or separately once on single audio events, to establish subject classification 502, and on a balanced batch of audio samples from different events or conditions to maximize the cross-correlation 504. The overall optimization function includes weight parameters to define the trade-off between the two objectives. While the process is not specifically intended for the purpose of user authentication, the embedding model 316 can be trained and optimized for very high specificity, in order to avoid capturing false data or being tricked by malicious attacks.

The embedding model 316 (which can be represented as $M_e$) includes the trained neural network. The audio embeddings 318 ($E_e^x$) are extracted as a vector based on the values of neurons within the trained neural network. The audio embeddings 318 (which, as discussed above, are extracted from the enrollment samples 312) are aggregated together and averaged to create the personalized match profile 324 ($MP_e$), as shown in Equation 3. The match profile 324 is used only for the specific audio event 306 (e) for which the enrollment samples 312 were provided and the embedding model 316 was trained.

$$\left.\begin{array}{c} X_e^1 \to M_e \to E_e^1 \\ \vdots \\ X_e^n \to M_e \to E_e^n \end{array}\right\} \to MP_e \quad (3)$$

$$\left.\begin{array}{c} X_t^1 \to M_t \to E_t^1 \\ \vdots \\ X_t^n \to M_t \to E_t^n \end{array}\right\} \to MP_t \quad (4)$$

In the case of cross-event match profile creation, a match profile 324 is created using the enrollment samples 312 for a source audio event 306 (e.g., speech) and then transformed into a match profile 324 for the target audio event (e.g., cough). Therefore, the enrollment stage 308 does not necessarily need samples of the target audio event (e.g., cough). The audio event detection operation 307 utilizes one or more modules for classifying and identifying the targeted type of audio event 306 (e.g., using supervised or unsupervised techniques). The audio event detection operation 307 provides information and one or more labels for the selection of the corresponding embedding model 316 or a transformer model for creation of the match profile 324 or subject verification.

The process 300 can use different approaches with different performances for cross-event match profile creation and transforming the embedding model 316. In some embodiments, the transformation of the embedding model 316 includes capturing the mapping between the common physiologically-correlated audio characteristics among different audio events of the subject 301.

Figure 6A:
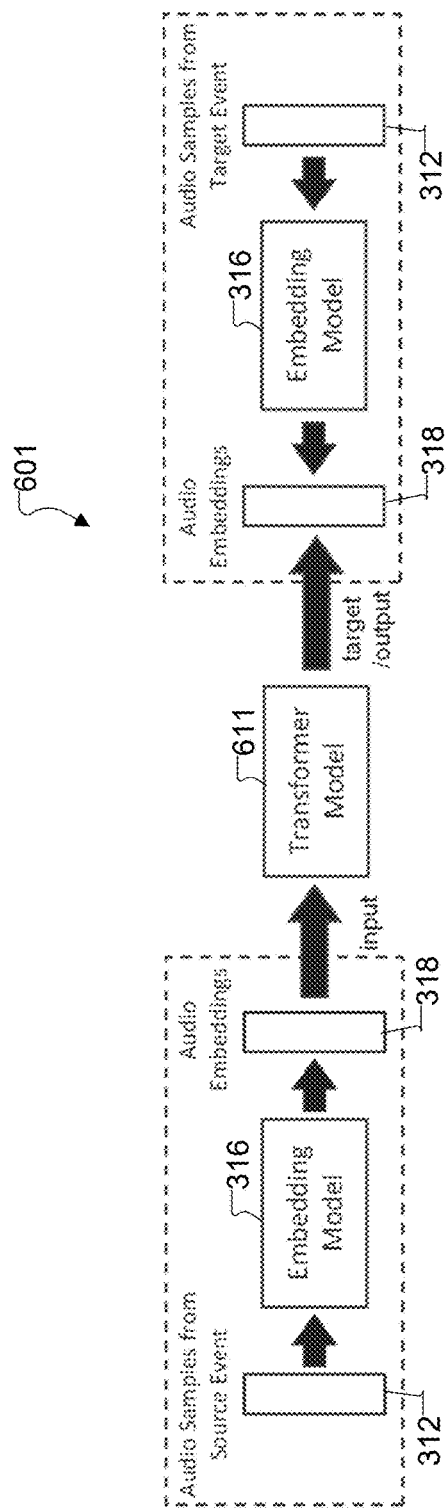
FIGS. 6A and 6B illustrate example processes for training and optimizing a transformer model in accordance with this disclosure.
Figure 6B:
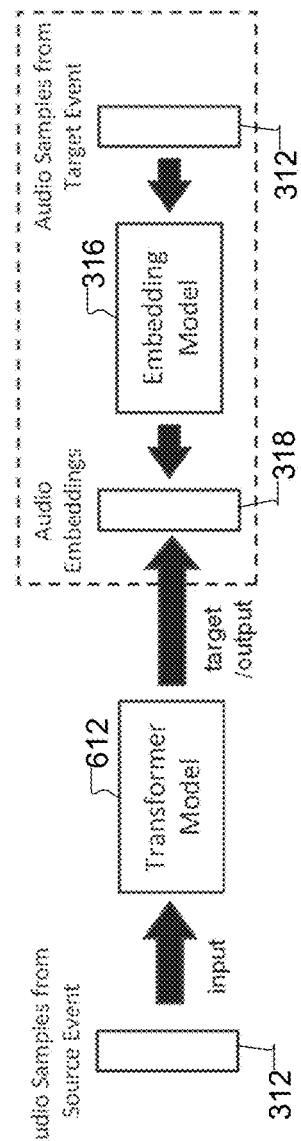

FIGS. 6A and 6B illustrate example processes 601-602 for training and optimizing a transformer model in accordance with this disclosure. As shown in FIG. 6A, a transformer model 611 ($M_{et}$) is trained and optimized offline such that it maps and converts the audio embeddings 318 ($E_e^x$) of enrollment samples 312 for an enrollment event (e) to audio embeddings 318 ($E_t^x$) for a target event (t). The transformer model 611 combined with the previous embedding model 316 ($M_e$) are used to extract audio embeddings 318 of enrollment samples 312 for the target event. The audio embeddings 318 are aggregated to create a transformed match profile 324 ($MP_t'$) according to the following equation:

$$\left.\begin{array}{c} X_e^1 \to M_e \to M_{et} \to E_t^1 \\ \vdots \\ X_e^n \to M_e \to M_{et} \to E_t^n \end{array}\right\} \to MP_t' \quad (5)$$

Alternatively, the same transformer model 611 ($M_{et}$) can be applied to the firstly created match profile 324 ($MP_e$), according to the following equation:

$$\left.\begin{array}{c} X_e^1 \to M_e \to E_e^1 \\ \vdots \\ X_e^n \to M_e \to E_e^n \end{array}\right\} \to MP_e \to M_{et} \to MP_t' \quad (6)$$

Using the process 601, the transformer model 611 is trained using the audio embeddings 318 extracted from the training dataset, utilizing the already trained embedding model 316 for the source and target events.

As shown in FIG. 6B, a transformer model 612 (M'$_{et}$) is trained and optimized offline such that it maps and extracts audio embeddings 318 (E$_t^x$) of a target event directly from enrollment samples 312 (X$_e^x$) of the enrollment event. The transformer model 612 (M'$_{et}$) is then used to directly extract audio embeddings 318 of enrollment samples 312 for the target event. The audio embeddings 318 are aggregated to create a transformed match profile 324 (MP'$_t$) according to the following equation:

$$\left.\begin{array}{c} X_e^1 \to M'_{et} \to E_t^1 \\ \vdots \\ X_e^n \to M'_{et} \to E_t^n \end{array}\right\} \to MP'_t \quad (7)$$

Using the process 602, the transformer model 612 is trained using the audio samples from the training set and their corresponding audio embeddings 318 for the target event, utilizing the already trained embedding model 316 for the target event.

Figure 7:
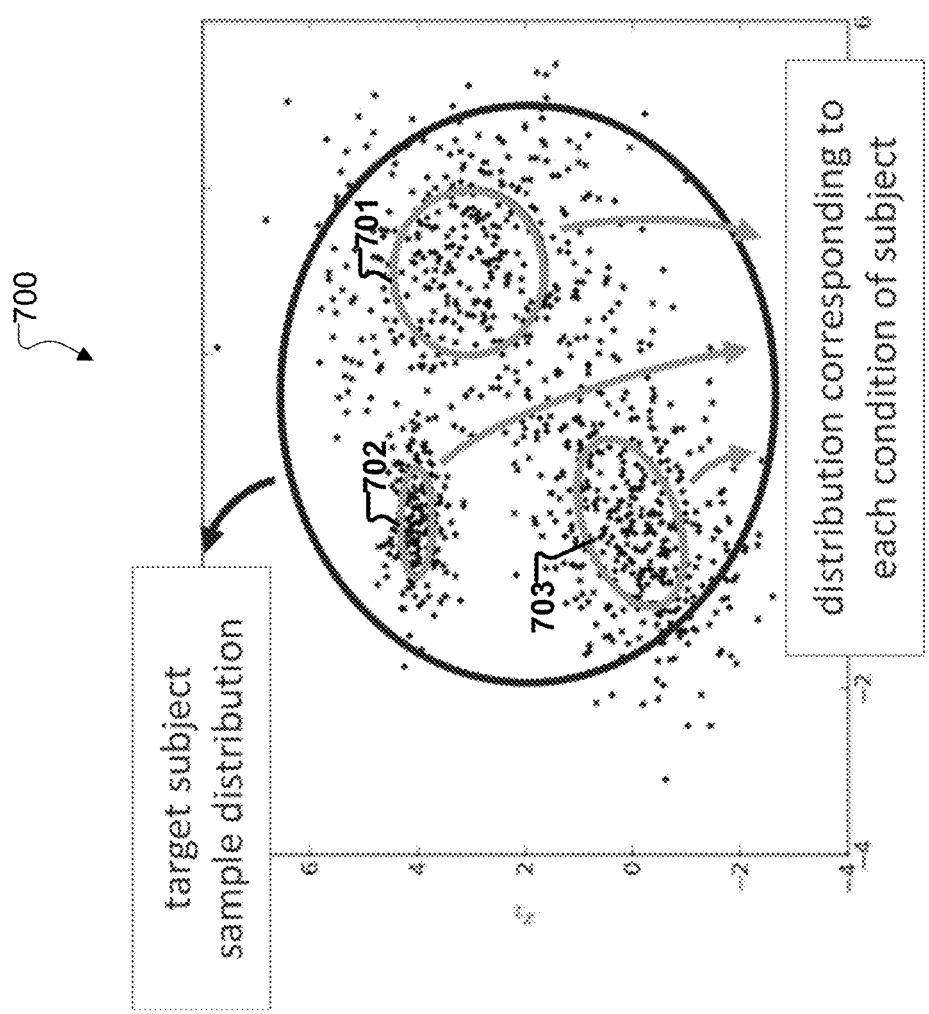
FIG. 7 illustrates an example plot showing distribution of audio embeddings from a target subject for different conditions in accordance with this disclosure.

The evaluated audio embeddings 318 can be influenced by a change in condition of the subject 301. As discussed above, the embedding model 316 is optimized with the objective of minimizing the variation caused by different conditions of the subject 301. In some embodiments, an unsupervised machine learning model (e.g., GMM) can be integrated into prediction to consider the variation of subject condition. The unsupervised layer, which can follow the embedding model 316, is trained to cluster audio embeddings 318 corresponding to one condition and map them to a distribution (e.g., a Gaussian distribution). The match profile 324 stores the properties of these distributions based on the aggregation of audio embeddings 318 and provides separate distributions for various subject conditions using the added unsupervised layer. For example, FIG. 7 illustrates an example plot 700 showing distribution of audio embeddings from a target subject for different conditions. In FIG. 7, the ovals 701-703 indicate different distributions of audio embeddings 318 corresponding to different conditions. The conditional probability is then used to capture multiple subject conditions and provide accurate un-biased prediction for subject verification. The trained embedding model 316 and conditional prediction model reduce the bias towards a specific subject condition. As a result, the embedding model 316, the evaluated audio embeddings 318, and the match profile 324 become resilient against changes in condition of the subject 301.

Due to possible gradual changes in human physiological structure and vocal cords, the performance of the match profile 324 may degrade over time. The process 300 can update the match profile 324 by learning from the audio segments 326 that continue to be collected over time. The passively collected audio segments 326 lack the ground truth of subject identity. Therefore, to prevent the embedding model 316 being trained on wrong data, the match profile 324 is updated only using the audio segments 326 that have a very limited distance to the match profile 324 with high probability of belonging to the subject 301. For example, a threshold can be created for each subject condition (shown as ovals in FIG. 7). If the distance of the extracted audio embeddings 318 from the newly collected audio segments 326 is smaller than the corresponding threshold, then the embedding model 316 is updated with the new audio segments 326. The distance threshold is defined during the offline training 320 of the embedding model 316 and any conditional prediction models when distribution properties of audio embeddings 318 related to subject conditions are evaluated.

In an embodiment of the process 300, physiological characteristics of the subject 301 can be modeled and updated using continuously collected audio. The physiological characteristics, which are unique to the subject 301, are evaluated at run time 310 and stored for further analysis such as health diagnosis, subject classification, and the like. In this embodiment, a separate match profile 324 can be defined separately for each specific audio event 306. For example, the physiological characteristics of the subject 301 with regards to cough or speech events can be used as additional features in cough or speech-based obstruction severity estimation.

In this embodiment, enrollment samples 312 from the subject 301 are used to create the match profile 324. The match profile 324 is stored as a set of features correlated with physiological characteristics of the subject 301, instead of being used for subject verification. Therefore, subject verification and audio collection do not need to be performed. The operations performed in modeling the physiological characteristics of the subject 301 are similar to those of audio collection: the enrollment samples 312 are collected and processed to extract the audio embeddings 318, and the audio embeddings 318 are aggregated and stored as the match profile 324. The match profile 324 can be updated continuously by collecting new audio segments 326 from the subject 301.

In another embodiment of the process 300, passive audio collection specific for the subject 301 can be implemented for a scenario where the condition of the subject 301 does not change. For example, during a medical appointment in a clinic setting, where audio of the subject 301 only needs to be recorded during the appointment while being examined by a medical professional, the condition of the subject 301 is assumed to be consistent. In this scenario, the process 300 can collect and verify the audio from the subject 301 by automatic enrollment of the subject 301.

In this embodiment, the embedding model 316 and match profile 324 are statically defined and created by the provided enrollment samples 312 in the audio recording 304 of the current static condition. After the enrollment stage 308, one or more specified audio events 306 in collected audio segments 326 of the subject 301 are verified and checked against the match profile 324 to determine whether they belong to the subject 301. In addition, in case the recording environment changes or the subject 301 demonstrates multiple variations of an audio event 306, the process 300 can handle the changes and provide an unbiased and consistent prediction, due to its resiliency and adaptiveness to changing conditions of the subject 301.

In another embodiment of the process 300, subject identities of a given set of audio samples are estimated and annotated using an automatic audio annotation tool. The audio samples could be segmented in advance by a third-party module or entity. The labels of subject identity provided for the audio samples are stored as annotation instead of storing the subject-specific audio samples.

In this embodiment, the embedding model 316 and match profile 324 are statically defined and created using a subset of the provided audio samples. The operations performed in the automatic annotation are similar to those of audio collection. During the enrollment stage 308, the match profile 324 is created given a set of samples. At run time 310, provided audio segments 326 by the subject 301 are verified and checked against the match profile 324 to determine whether they belong to the subject 301.

In some embodiments, a set of distinct match profiles 324 can be created by enrolling multiple specific subjects 301 in order to collect and verify their audio individually and simultaneously on the same device. For example, the process 300 could be performed multiple times for multiple subjects 301 on the same smart device to monitor and track health condition for multiple members of a household.

As discussed above, the audio events 306 that are generated from the subject 301, such as a cough or speech, contain certain audio characteristics that have high correlation with the physiological (e.g., lung) structure and/or respiratory condition of the subject 301. One or more of these audio characteristics and their combination have been shown to be unique for each person such that they can be utilized for identifying the subject 301. These audio characteristics can be extracted and evaluated by analyzing energy, time-frequency domain, and amplitude variation of the audio segments 326. These variables and their derivatives (e.g., mean, median, time derivatives, minimum, maximum, and the like) are calculated and used as audio features 314, which uniquely correlate with the physiological structure of the subject 301, such as properties of lung, respiratory airways, vocal tract, etc.

In some embodiments, in order to calculate audio features 314 in the frequency spectrum, the spectrum is divided into multiple (e.g., 10-13) regions (e.g., Mel banks), which have prominent and distinctive audio characteristics. These regions or frequency banks can define the range for the Mel Frequency Cepstral Coefficient (MFCC) values, as shown in Table 1 below. It is observed that combining the MFCC features and their derivatives provides distinctive features that correlate with the physiological structure of the subject 301 and identifies speakers using multiple audio event types, such as speech, cough, etc.

TABLE 1

Audio Frequency Range Corresponding with MFCC Audio Characteristics

| MFCC | Audio Frequency Range | | |
|---|---|---|---|
| | Start | Peak | End |
| 0 | 300.00 | 517.33 | 781.90 |
| 1 | 517.33 | 781.90 | 1103.97 |
| 2 | 781.90 | 1103.97 | 1496.04 |
| 3 | 1103.97 | 1496.04 | 1973.32 |
| 4 | 1496.04 | 1973.32 | 2554.33 |
| 5 | 1973.32 | 2554.33 | 3261.62 |
| 6 | 2554.33 | 3261.62 | 4122.63 |
| 7 | 3261.62 | 4122.63 | 5170.76 |
| 8 | 4122.63 | 5170.76 | 6446.70 |
| 9 | 5170.76 | 6446.70 | 8000.00 |

Table 2 below summarizes some of the audio features 314 that have high correlation with different aspects of physiological structure, its respective biomarker and description. The audio features 314 extracted from energy, pressure, and low channel MFCC have shown high correlation with the speed and volume of air exchange during speech, cough, sneeze, wheeze, etc., which are indicators of body size, lung capacity, respiratory airway opening area, etc. One level higher MFCC features, audio pitch, shimmer, and jitter have shown high correlation with the amount of restrictions in the airway and properties of vocal tract. These physiological biomarkers and properties are among the unique audio features 314 that can be extracted and used in identifying the subject 301 based on multiple of types of audio events 306, such as speech, cough, etc.

TABLE 2

Audio Features and Characteristics Correlated with Physiological Structure of the Subjects

| | Physiological Correlation | |
|---|---|---|
| Audio Characteristics | Biomarker | Description |
| Energy, Pressure level, MFCC_0, MFCC_1, MFCC_2, ZCR | FEV, FIF, FVC | Body size, lung capacity |
| Energy, Pressure level, MFCC_0, MFCC_1, MFCC_2, ZCR | FEV1, FEV1/FVC, PEF, subglottal pressure | Body size, airway opening area |
| Pitch, Spectral Centroid, Flux, MFCC_2, MFCC_3, Shimmer, Jitter | Wheezing intensity | Airway restriction |
| Pitch, Spectral Centroid, Shimmer, Jitter | Fundamental frequency | Body size, properties of vocal tract |

FEV: Forced Expiratory Volume
FIF: Forced Inspiratory Volume
FEV1: Forced Expiratory Volume in 1 Second
FVC: Forced Vital Capacity (lung capacity)
FEV1/FVC: Severity of Airway Obstruction
PEF: Peak Exhalation Flow
ZCR: Zero Crossing Rate
Pitch: Ordering of audio in frequency scale
MFCC: Mel Frequency Cepstral Coefficient
Spectral Centroid: Center of mass in audio spectrum
Spectral Flux: change in center of mass in audio spectrum
Jitter: measure of audio frequency instability
Shimmer: measure of audio amplitude instability As described above, the process 300 provides a number of advantageous features over conventional monitoring techniques. For example, the process 300 provides event-independent audio-based subject verification. That is, the process 300 provides label data for the passively-detected audio segments 326, which identifies whether or not the audio segments 326 belong to the subject 301. The subject verification process happens passively using short frames of audio without interaction or prior trigger from the subject 301 (i.e., no command word is needed). The process 300 implements the match profile 324, which is audio event-independent. Thus, one or more types of audio events 306 can be collected and verified requiring no prior data or only a limited set of prior data for the corresponding events.

The process 300 also features physiologically-correlated, subject-distinctive audio embeddings. As discussed above, the process 300 utilizes a personal match profile 324, which is created during the enrollment stage 308 using a limited number of enrollment samples 312 from the subject 301. The match profile 324 leverages the audio embeddings 318 to extract audio features 314 that distinguish the samples of audio events 306 from different subjects. The embedding model 316 is trained to learn and evaluate the audio embeddings 318 by focusing on the audio features 314 within the audio segments 326, which are correlated with the physiological structure of the subject 301. Utilization of the audio embeddings 318 reduces the volume of sample data used during the enrollment stage 308 since the match profile 324 focuses on a more specific set of physiologically-correlated audio features 314 to distinguish between subjects. This enables the process 300 to be further independent from the recording device and environment. Thus, the process 300 can be implemented on one or more personal electronic devices for a wider range of subject-specific monitoring.

The process 300 also features cross-event match profile creation to extend the audio collection and subject verification capability to multiple audio events. As discussed above, a match profile 324 for a specific target audio event 306 can be created during the enrollment stage 308 using enrollment samples 312 of another source audio event or by transforming its match profile 324. The transformed match profile 324 can be used to verify identity of the specific target audio event 306. The embedding model 316 is trained such that it captures and maps physiologically-correlated audio embeddings that are common across different audio events 306. The embedding model 316 can be used to transform the audio embeddings 318 and the match profile 324 of the source audio event 306 to the target audio event 306. This eliminates the need for a large and comprehensive dataset from the subject 301 for all target audio events 306. It further eliminates the inconvenience for the subject 301 to provide samples of certain challenging audio events 306 (e.g., cough samples from a subject with chronic pulmonary condition).

In addition, the process 300 features resiliency and adaptiveness to changing conditions of the subject 301. Such changes can affect the audio characteristics and thereby influence subject verification accuracy. As discussed above, the match profile 324 is created such that the audio features 314 that are primarily affected by passage of time or by changes in subject condition are selected and deprioritized in the audio embeddings 318. The subject verification decision is made by learning and considering various distributions of the condition of the subject 301 to become generalizable. Also, with additional data captured at run time 310, the match profile 324 can adapt to gradual changes in the condition of the subject 301.

Although FIG. 3 illustrates one example of a process 300 for passive subject specific monitoring, various changes may be made to FIG. 3. For example, various operations in FIG. 3 could overlap, occur in parallel, occur in a different order, or occur any number of times. Also, the various functions and operations shown and described above with respect to FIG. 3 can be implemented in the electronic device (which could include any of the electronic devices 101, 102, 104 or the server 106) in any suitable manner. For example, in some embodiments, at least some of the functions and operations can be implemented or supported using one or more software applications or other software instructions that are executed by the processor(s) 120, 240 of the electronic device(s). In other embodiments, at least some of the functions and operations can be implemented or supported using dedicated hardware components. In general, the functions and operations can be performed using any suitable hardware or any suitable combination of hardware and software/firmware instructions. In general, computing and communication systems come in a wide variety of configurations, and FIG. 3 does not limit the scope of this disclosure to any particular configuration.

Figure 8:
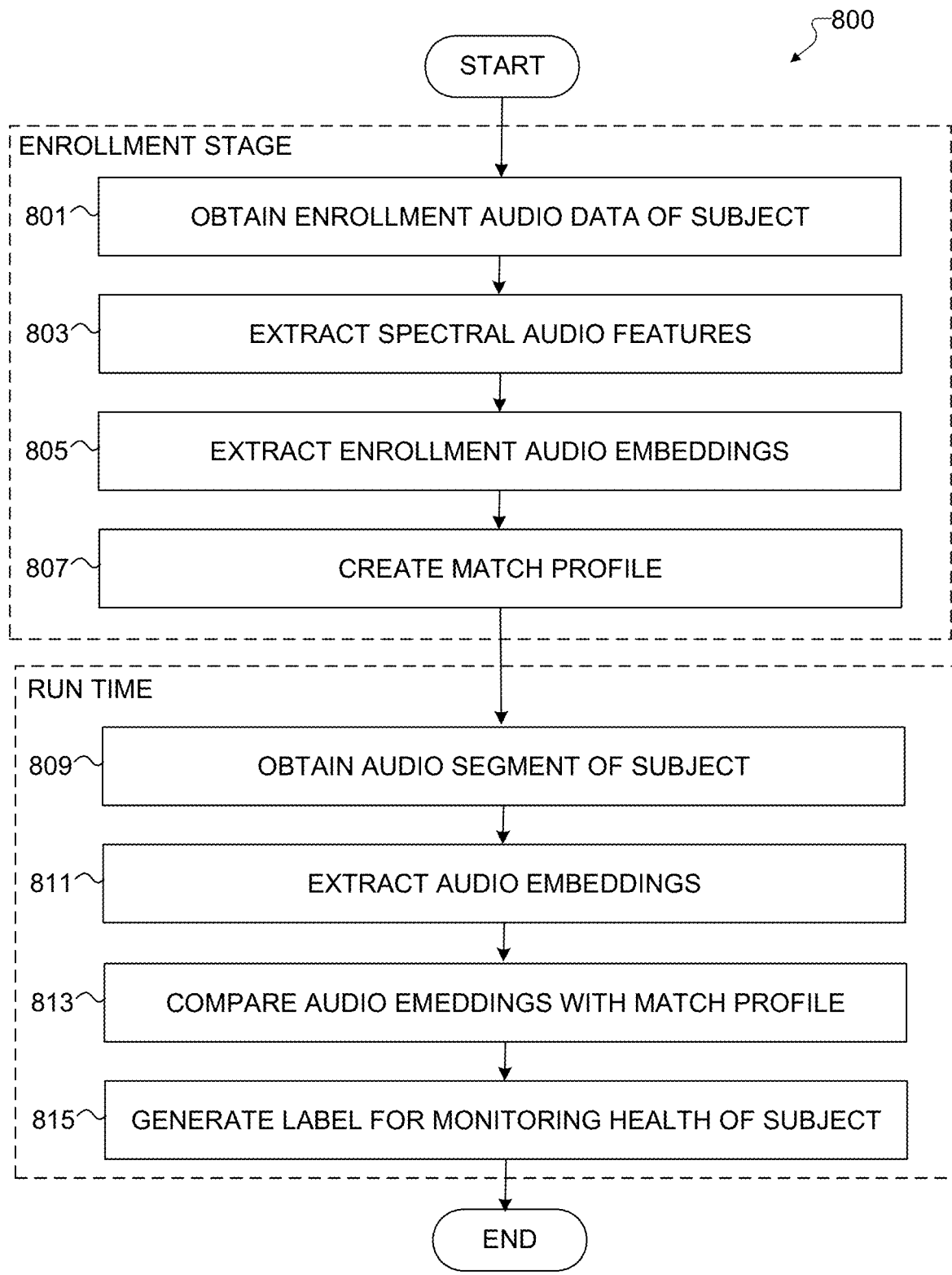
FIG. 8 illustrates an example method for passive subject specific monitoring in accordance with this disclosure.

FIG. 8 illustrates an example method 800 for passive subject specific monitoring in accordance with this disclosure. For ease of explanation, the method 800 shown in FIG. 8 is described as involving the process 300 shown in FIG. 3. The method 800 may be performed by an electronic device, such as the electronic device 101 of FIG. 1. However, the method 800 could involve any other suitable process and be performed by any suitable device or system without departing from the scope of this disclosure.

During operations 801-807, the electronic device performs an enrollment stage.

At operation 801, enrollment audio data of a target subject is obtained. The enrollment audio data includes samples of one or more enrollment audio events of the target subject. The enrollment audio events can include a cough, a sneeze, or a speech, another suitable audio event, or a combination of these. This can include, for example, the electronic device 101 obtaining audio recordings 304 of the subject 301 that include one or more audio events 306.

At operation 803, the samples are processed to extract one or more spectral audio features. This can include, for example, the electronic device 101 processing the enrollment samples 312 to extract one or more spectral audio features 314.

At operation 805, enrollment audio embeddings associated with the target subject are extracted from the one or more enrollment audio events using an embedding model. The embedding model is a trained machine learning model. The embedding model transforms the spectral audio features to the enrollment audio embeddings in order to correlate the enrollment audio data with a physiological structure of the target subject. This can include, for example, the electronic device 101 extracting the enrollment audio embeddings 318 from the enrollment audio events 306 using the embedding model 316.

At operation 807, a match profile of the target subject is created using the extracted enrollment audio embeddings. This can include, for example, the electronic device 101 creating the match profile 324 using the enrollment audio embeddings 318. In some embodiments, the electronic device 101 can create a second match profile 324 by transforming the match profile 324, wherein the match profile 324 corresponds to a first audio event 306 of the subject 301 and the second match profile corresponds to a second audio event 306 of the subject 301.

After the enrollment stage, the electronic device performs operations 809-815 in a run time environment.

At step 809, an audio segment comprising one or more audio events of the target subject is obtained. This can include, for example, the electronic device 101 obtaining an audio segment 326 comprising one or more audio events 306 of the subject 301.

At step 811, audio embeddings from the one or more audio events are extracted using the embedding model. This can include, for example, the electronic device 101 extracting audio embeddings 318 from the one or more audio events 306 using the embedding model 316.

At step 813, the extracted audio embeddings are compared with the match profile of the target subject. This can include, for example, the electronic device 101 comparing the extracted audio embeddings 318 with the match profile 324. In particular, the electronic device 101 can evaluate one or more distancing metrics 328 between the audio embeddings 318 and the match profile 324.

At step 815, a first label or a second label is generated for the audio segment based on whether or not the extracted audio embeddings match the match profile. The first label or the second label enables correlation of the audio segment with the target subject for monitoring a health condition of the target subject. This can include, for example, the electronic device 101 generating a "match" label 332 or a "no match" label 334 for the audio segment 326 based on whether or not the extracted audio embeddings 318 match the match profile 324.

Although FIG. 8 illustrates one example of a method 800 for passive subject specific monitoring, various changes can be made to FIG. 8. For example, various steps in FIG. 8 could overlap, occur in parallel, occur serially, occur in a different order, or occur any number of times. Also, the steps of the method 800 could be implemented in any suitable manner, such as entirely within the electronic device 101 or using a combination of devices. For instance, as indicated above, electronic device 101 could collect data and provide the data to a server 106, which could then process the data and generate any suitable output.

The embodiments disclosed herein provide a system that can be used for reliable audio collection from a specific target subject for mobile health monitoring. The disclosed system is robust and adaptive such that it handles background noise and changing conditions of the subjects and is applicable to any smart device (e.g. smart phone, wearable, hearable, smart speaker, and the like) to extend the coverage of reliable monitoring. The system uses a very limited set of data from the subject to improve the convenience of enrolling. Monitoring can occur passively without any interaction from the user. Furthermore, the system passively provides a privacy-preserved monitoring of the specific subject.

Applications for the disclosed embodiments can include various health assessments, including lung health assessment. However, possible applications are not limited to health assessments. The disclosed embodiments for passive monitoring are applicable for any assessment that benefits from using non-speech audio activities within a recorded audio. Some examples include analyzing vocal cord dysfunction, cognitive impairment in subjects, dementia, anxiety/stress, or classification of environment sounds and locations.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method comprising:
obtaining, by an electronic device, an audio segment comprising one or more audio events of a target subject;
extracting, by the electronic device, audio embeddings from the one or more audio events using an embedding model, the embedding model comprising a machine learning model that is trained to maximize cross-correlation of evaluated audio embeddings generated during training and focus on audio features common across different conditions of subjects such that the embedding model is resilient against changes in condition of the target subject, wherein the embedding model extracts the audio embeddings in order to correlate the one or more audio events with a physiological structure of the target subject;
comparing, by the electronic device, the extracted audio embeddings with a match profile of the target subject, the match profile generated during an enrollment stage;
generating, by the electronic device, a label for the audio segment based on whether or not the extracted audio embeddings match the match profile, wherein the label enables correlation of the audio segment with the target subject for monitoring a health condition of the target subject; and
in response to determining that a distance of the extracted audio embeddings from the match profile is smaller than a specified threshold, updating the match profile using the audio segment.

2. The method of claim 1, further comprising:
performing the enrollment stage by the electronic device by:
obtaining enrollment audio data of the target subject, the enrollment audio data comprising samples of one or more enrollment audio events of the target subject;
extracting enrollment audio embeddings associated with the target subject from the one or more enrollment audio events using the embedding model; and
creating the match profile of the target subject using the extracted enrollment audio embeddings.

3. The method of claim 2, wherein:
the samples are processed to extract one or more spectral audio features; and
the embedding model transforms the spectral audio features into the enrollment audio embeddings in order to correlate the enrollment audio data with the physiological structure of the target subject.

4. The method of claim 3, wherein:
the match profile of the target subject comprises a first match profile; and
performing the enrollment stage further comprises:
creating a second match profile by transforming the first match profile, wherein the first match profile corresponds to a first audio event of the target subject and the second match profile corresponds to a second audio event of the target subject.

5. The method of claim 1, wherein comparing the extracted audio embeddings with the match profile of the target subject comprises evaluating one or more distancing metrics.

6. The method of claim 1, wherein the audio segment comprises audio data received from multiple devices.

7. The method of claim 1, wherein the one or more audio events comprise at least one of a cough, a sneeze, or a speech of the target subject.

8. An electronic device comprising:
at least one memory configured to store instructions; and
at least one processor configured when executing the instructions to:
obtain an audio segment comprising one or more audio events of a target subject;
extract audio embeddings from the one or more audio events using an embedding model, the embedding model comprising a machine learning model that is trained to maximize cross-correlation of evaluated audio embeddings generated during training and focus on audio features common across different conditions of subjects such that the embedding model is resilient against changes in condition of the target subject, wherein the embedding model extracts the audio embeddings in order to correlate the one or more audio events with a physiological structure of the target subject;
compare the extracted audio embeddings with a match profile of the target subject, the match profile generated during an enrollment stage;
generate a label for the audio segment based on whether or not the extracted audio embeddings match the match profile, wherein the label enables correlation of the audio segment with the target subject for monitoring a health condition of the target subject; and
in response to determining that a distance of the extracted audio embeddings from the match profile is smaller than a specified threshold, update the match profile using the audio segment.

9. The electronic device of claim 8, wherein:
the at least one processor is further configured to perform the enrollment stage; and
to perform the enrollment stage, the at least one processor is configured to:
  obtain enrollment audio data of the target subject, the enrollment audio data comprising samples of one or more enrollment audio events of the target subject;
  extract enrollment audio embeddings associated with the target subject from the one or more enrollment audio events using the embedding model; and
  create the match profile of the target subject using the extracted enrollment audio embeddings.

10. The electronic device of claim 9, wherein the at least one processor is further configured to:
process the samples to extract one or more spectral audio features; and
use the embedding model to transform the spectral audio features into the enrollment audio embeddings in order to correlate the enrollment audio data with the physiological structure of the target subject.

11. The electronic device of claim 10, wherein:
the match profile of the target subject comprises a first match profile; and
to perform the enrollment stage, the at least one processor is configured to:
  create a second match profile by transforming the first match profile, wherein the first match profile corresponds to a first audio event of the target subject and the second match profile corresponds to a second audio event of the target subject.

12. The electronic device of claim 8, wherein, to compare the extracted audio embeddings with the match profile of the target subject, the at least one processor is configured to evaluate one or more distancing metrics.

13. The electronic device of claim 8, wherein the audio segment comprises audio data received from multiple devices.

14. The electronic device of claim 8, wherein the one or more audio events comprise at least one of a cough, a sneeze, or a speech of the target subject.

15. A non-transitory computer readable medium containing computer readable program code that, when executed, causes at least one processor of an electronic device to:
obtain an audio segment comprising one or more audio events of a target subject;
extract audio embeddings from the one or more audio events using an embedding model, the embedding model comprising a machine learning model that is trained to maximize cross-correlation of evaluated audio embeddings generated during training and focus on audio features common across different conditions of subjects such that the embedding model is resilient against changes in condition of the target subject, wherein the embedding model extracts the audio embeddings in order to correlate the one or more audio events with a physiological structure of the target subject;
compare the extracted audio embeddings with a match profile of the target subject, the match profile generated during an enrollment stage;
generate a label for the audio segment based on whether or not the extracted audio embeddings match the match profile, wherein the label enables correlation of the audio segment with the target subject for monitoring a health condition of the target subject; and
in response to determining that a distance of the extracted audio embeddings from the match profile is smaller than a specified threshold, update the match profile using the audio segment.

16. The non-transitory computer readable medium of claim 15, further containing computer readable program code that when executed causes the at least one processor to perform the enrollment stage;
wherein the computer readable program code that when executed causes the at least one processor to perform the enrollment stage comprises computer readable program code that when executed causes the at least one processor to:
  obtain enrollment audio data of the target subject, the enrollment audio data comprising samples of one or more enrollment audio events of the target subject;
  extract enrollment audio embeddings associated with the target subject from the one or more enrollment audio events using the embedding model; and
  create the match profile of the target subject using the extracted enrollment audio embeddings.

17. The non-transitory computer readable medium of claim 16, further containing computer readable program code that when executed causes the at least one processor to:
process the samples to extract one or more spectral audio features; and
use the embedding model to transform the spectral audio features to the enrollment audio embeddings in order to correlate the enrollment audio data with the physiological structure of the target subject.

18. The non-transitory computer readable medium of claim 17, wherein:
the match profile of the target subject comprises a first match profile; and
the computer readable program code that when executed causes the at least one processor to perform the enrollment stage comprises:
  computer readable program code that when executed causes the at least one processor is to create a second match profile by transforming the first match profile, wherein the first match profile corresponds to a first audio event of the target subject and the second match profile corresponds to a second audio event of the target subject.

19. The non-transitory computer readable medium of claim 15, wherein the computer readable program code that when executed causes the at least one processor to compare the extracted audio embeddings with the match profile of the target subject comprises:
computer readable program code that when executed causes the at least one processor to evaluate one or more distancing metrics.

20. The non-transitory computer readable medium of claim 15, wherein the one or more audio events comprise at least one of a cough, a sneeze, or a speech of the target subject.

* * * * *